(12) United States Patent
Schmidt et al.

(10) Patent No.: US 7,522,811 B2
(45) Date of Patent: Apr. 21, 2009

(54) PRODUCING SANDWICH WAVEGUIDES

(75) Inventors: Oliver Schmidt, Palo Alto, CA (US);
Michael Bassler, Menlo Park, CA (US);
Peter Kiesel, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 11/777,661

(22) Filed: Jul. 13, 2007

(65) Prior Publication Data

US 2009/0016690 A1     Jan. 15, 2009

(51) Int. Cl.
*G02B 6/10* (2006.01)
(52) U.S. Cl. .................. 385/146; 385/129; 385/130
(58) Field of Classification Search ................ 385/130, 385/146, 129
See application file for complete search history.

(56) References Cited

U.S. PATENT DOCUMENTS

| | | | |
|---|---|---|---|
| 3,797,911 A | 3/1974 | Kogeinik et al. | |
| 4,715,672 A | 12/1987 | Duguay et al. | |
| 5,281,305 A | 1/1994 | Lee et al. | |
| 5,370,842 A | 12/1994 | Mizazaki et al. | |
| 5,572,328 A | 11/1996 | Fouckhardt et al. | |
| 6,108,463 A | 8/2000 | Herron et al. | |
| 6,192,168 B1 | 2/2001 | Feldstein et al. | |
| 6,483,959 B1 | 11/2002 | Singh et al. | |
| 6,490,034 B1 | 12/2002 | Woias et al. | |
| 6,558,945 B1 | 5/2003 | Kao | |
| 6,577,780 B2 | 6/2003 | Lockhart | |
| 6,580,507 B2 | 6/2003 | Fry et al. | |
| 6,800,849 B2 | 10/2004 | Staats | |
| 6,856,718 B2 | 2/2005 | Kane et al. | |
| 6,934,435 B2 | 8/2005 | Kane | |

(Continued)

FOREIGN PATENT DOCUMENTS

WO     WO 00/62050     10/2000

(Continued)

OTHER PUBLICATIONS

Weismann, R., Kalveram, S., Rudolph, S., Johnck, M., and Neyer, A., "Singlemode polymer waveguides for optical backplanes," Electronics Letters, vol. 32, No. 25, Dec. 5, 1996, pp. 2329-2330.

(Continued)

*Primary Examiner*—Jennifer Doan
(74) *Attorney, Agent, or Firm*—Leading-Edge Law Group, PLC; James T. Beran

(57) ABSTRACT

Complementary surface fabrication processes such as molding, casting, embossing, and so forth, are used to produce articles, structures, or components structured to operate as sandwich waveguides. Resulting complementary surface artifacts include, for example, optical quality surfaces on wall parts, other exposed artifacts that occur where a complementary solid surface contacts non-solid material during fabrication, and sub-surface artifacts such as integrally formed connections between wall parts and base parts. A body whose surface includes a waveguide's inward surfaces, outward surfaces, and light interface surfaces to receive incident light can be formed in a single step, leaving a partially bounded fluidic region that can then be covered to provide a channel that is bounded along a length yet open at its ends; other fluidic, electrical, and optical components can also be attached.

29 Claims, 10 Drawing Sheets

U.S. PATENT DOCUMENTS

| | | | |
|---|---|---|---|
| 7,046,357 | B2 | 5/2006 | Weinberger et al. |
| 7,064,836 | B2 | 6/2006 | Bechtel et al. |
| 7,195,465 | B2 | 3/2007 | Kane et al. |
| 7,248,361 | B2 | 7/2007 | Kiesel et al. |
| 7,268,868 | B2 | 9/2007 | Kiesel et al. |
| 7,358,476 | B2 | 4/2008 | Kiesel et al. |
| 7,386,199 | B2 | 6/2008 | Schmidt et al. |
| 7,456,953 | B2 | 11/2008 | Schmidt et al. |
| 7,479,625 | B2 | 1/2009 | Kiesel et al. |
| 2002/0155485 | A1 | 10/2002 | Kao |
| 2003/0020915 | A1 | 1/2003 | Schueller et al. |
| 2003/0081302 | A1 | 5/2003 | Kane et al. |
| 2003/0235924 | A1 | 12/2003 | Adams et al. |
| 2004/0038386 | A1 | 2/2004 | Zesch et al. |
| 2004/0109659 | A1 | 6/2004 | Aylward et al. |
| 2004/0175734 | A1 | 9/2004 | Stahler et al. |
| 2004/0178523 | A1 | 9/2004 | Kim et al. |
| 2004/0252957 | A1 | 12/2004 | Schmidt et al. |
| 2005/0084203 | A1 | 4/2005 | Kane |
| 2005/0249605 | A1 | 11/2005 | Kane et al. |
| 2006/0092413 | A1 | 5/2006 | Kiesel et al. |
| 2006/0193550 | A1 | 8/2006 | Wawro et al. |
| 2006/0268260 | A1 | 11/2006 | Liu et al. |
| 2007/0070347 | A1 | 3/2007 | Scherer et al. |
| 2007/0116609 | A1 | 5/2007 | Baeurle et al. |
| 2007/0145236 | A1 | 6/2007 | Kiesel et al. |
| 2007/0145249 | A1 | 6/2007 | Kiesel et al. |
| 2007/0146701 | A1 | 6/2007 | Kiesel et al. |
| 2007/0146704 | A1 | 6/2007 | Schmidt et al. |
| 2007/0146888 | A1 | 6/2007 | Schmidt et al. |
| 2007/0147189 | A1 | 6/2007 | Schmidt et al. |
| 2007/0147726 | A1 | 6/2007 | Kiesel et al. |
| 2007/0147728 | A1 | 6/2007 | Schmidt et al. |
| 2007/0148760 | A1 | 6/2007 | Klesel et al. |
| 2008/0013092 | A1 | 1/2008 | Maltezos et al. |
| 2008/0013877 | A1 | 1/2008 | Schmidt et al. |
| 2008/0197272 | A1 | 8/2008 | Kiesel et al. |
| 2009/0016672 | A1 | 1/2009 | Schmidt et al. |

FOREIGN PATENT DOCUMENTS

| | | |
|---|---|---|
| WO | WO 02/25269 A2 | 3/2002 |
| WO | WO 2005/108963 A1 | 11/2005 |

OTHER PUBLICATIONS

Kalvaram, S., and Neyer, A., "Precision moulding techniques for optical waveguide devices," SPIE, vol. 3135, 1997, pp. 2-11.

Becker, H., and Gartner, C., "Polymer microfabrication methods for microfluidic analytical applications," Electrophoresis, vol. 21, 2000, pp. 12-26.

Bernini, R., Campopiano, S., and Zeni, L., "Silicon Micromachined Hollow Optical Waveguides for Sensing Applications," IEEE Journal on Selected Topics in Quantum Electronics, vol. 8, No. 1, Jan./Feb. 2002, pp. 106-110.

Adams, M.L., Enzelberger, M., Quake, S., and Scherer, A., "Microfluidic integration on detector arrays for absorption and fluorescence micro-spectrometers," Sensors and Actuators A, vol. 104, 2003, pp. 25-31.

Singh, K., Liu, C., Capjack, C., Rozmus, W., and Backhouse, C.J., "Analysis of cellular structure by light scattering measurements in a new cytometer design based on a liquid-core waveguide," IEE Proc.-Nanobiotechnol., vol. 151, No. 1, Feb. 2004, pp. 10-16.

Kim, J.T., Choi, C.-G., Sung, H.-K., "Polymer-Planar-Lightwave-Circuit-Type Variable Optical Attenuator Fabricated by Hot Embossing Process," ETRI Journal, vol. 27, No. 1, Feb. 2005, pp. 122-125.

Schmidt, O., Bassler, M., Kiesel, P., Johnson, N.M., and Dohler, G.H., "Guiding light in fluids," Applied Physics Letters, vol. 88, 2006, 151109-1-151109-3.

Schmidt, O., Bassler, M., Kiesel, P., Johnson, N.M., and Dohler, G.H., "Enhanced light-target interaction using a novel anti-resonant waveguide concept," SPIE Proc. 6094, p. 80, 2006, 9 pages.

"4-Channel Optical Transceiver Applying 3-Dimensional Polymeric Waveguide," FIND, vol. 24, No. 4, 2006, pp. 1-5.

Univ. of Dortmund, "Polymeric integrated optic single-mode components-Industrial scale production technologies," printed from www-mst.e-technik.uni-dortmund.de—Mar. 21, 2007, 2 pg.

Schmidt, O., Bassler, M., Kiesel, P., Knollenberg, C., and Johnson, N., "Fluorescence Spectrometer-on-a-fluidic-chip," Lab Chip, 2007, DOI:10.1039/b618879f, 4 pages.

Goddard, N.J., Singh, K., Bounaira, F., Holmes, R.J., Baldock, S.J., Pickering, L.W., Fielden, P.R., and Snook, R.D., "Anti-Resonant Reflecting Optical Waveguides (Arrows), as Optimal Optical Detectors for MicroTAS Applications," printed from dias.umist.ac.uk on Aug. 1, 2005, pp. 1-5.

U.S. Appl. No. 11/777,712, submitted Jul. 13, 2007, 58 pages.

Notice of Allowance and Fee(s) Due in U.S. Appl. No. 12/098,584, mailed Oct. 6, 2008, 16 pages, published in PAIR.

PRODUCING SANDWICH WAVEGUIDES

This invention was made with Government support under contract N0001405-C-0430 awarded by the Office of Naval Research. The Government has certain rights in the invention.

This application is related to the following applications, each of which is hereby incorporated by reference in its entirety: "Anti-Resonant Waveguide Sensors", U.S. patent application No. 10/976,434, published as U.S. Patent Application Pub. No. 2006/0092413; "Fluorescence Reader Based on Anti-Resonant Waveguide Excitation", U.S. patent application Ser. No. 11/315,797; "Providing Light to Channels or Portions", U.S. patent application Ser. No. 11/316,660; "Producing Fluidic Waveguides", U.S. patent application Ser. No. 11/777,712; and "A Method and Apparatus for Improved Light Distribution in an Anti-Resonant Waveguide Sensor", U.S. patent application Ser. No. 11/777,976.

BACKGROUND OF THE INVENTION

The present invention relates generally to waveguide techniques, such as with waveguides in which facing surfaces are approximately parallel and separated by a region that can contain fluid.

U.S. Patent Application Publication No. 2006/0092413 describes anti-resonant waveguide sensors in which light is guided within a medium between a substrate and a covering layer both made from a transparent material such as glass; the transparent material has an index of refraction slightly higher than the medium, which can be a sample such as a thin film of liquid, gas, or aerosol carrying a target analyte. As a result, an anti-resonant wave can be generated in the medium in accordance with eigensolutions of a Helmholtz equation. Each eigensolution can be called an optical mode, and can be excited by directing a beam of light at the waveguide at a specific angle of incidence. The waveguide can have a tilted entrance facet to minimize reflection of an incident beam; other possible geometries include curved end facets and cylindrical sample shapes. A laser, a source of white light, or a light-emitting diode can provide the incident beam, while detectors can detect light propagating through the sample or scattered, refracted, or fluoresced by the sample, such as with wavelength sensitive elements.

Singh, K., Liu, C., Capjack, C., Rosmus, W., and Backhouse, J., "Analysis of cellular structure by light scattering measurements in a new cytometer design based on a liquid-core waveguide", IEEE Proc.-Nanobiotechnol., Vol. 151, No. 1, February 2004, pp. 10-16, describes a microfluidic optical cytometer used to generate and observe light scattered from biological cells. The cytometer includes a leaky waveguide, and an incoming laser beam can be coupled into the waveguide through a prism at an angle of incidence for a waveguide mode. A waveguide can include a microfluidic channel fabricated on a glass substrate with a glass superstrate, where the liquid microchannel can be a low index waveguide core 10-30 µm deep. One method to form a microchannel structure is to deposit a spin-coated or dip-coated polymer layer on the substrate, about 30 µm thick, and then pattern the layer with desired microchannels, about 1 mm in width. The superstrate is then bonded onto the patterned polymer layer, forming the microchannel waveguide structure. The polymer layer serves to separate the two glass slides, and is not illuminated; photoresist is particularly useful as the polymer layer. Images of scattered light can be taken using an optical microscope and a CCD camera, either to view an image of a cell or to obtain its characteristic scattering pattern.

It would be advantageous to have improved waveguide techniques.

SUMMARY OF THE INVENTION

The invention provides various exemplary embodiments, including products, methods, articles, and devices. In general, the embodiments involve articles, structures, parts, or components that can operate as waveguides.

These and other features and advantages of exemplary embodiments of the invention are described below with reference to the accompanying drawings.

DETAILED DESCRIPTION

Figure 1:
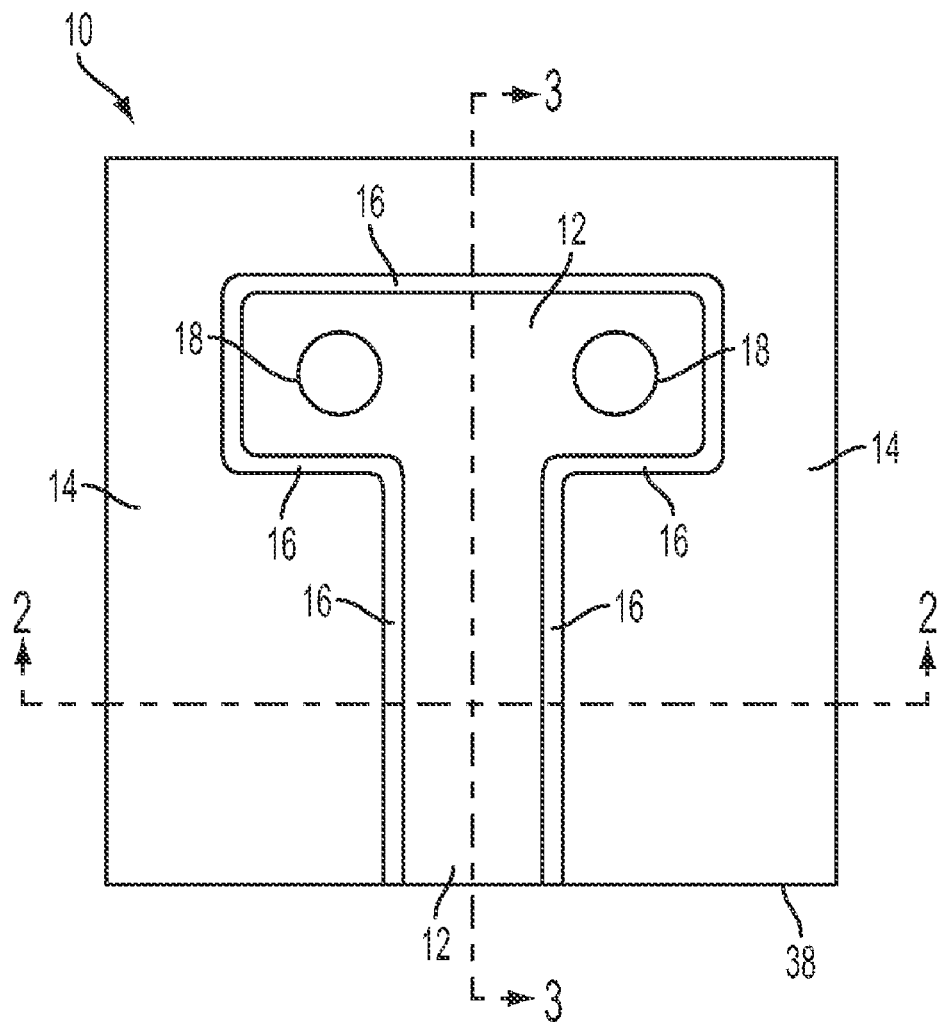
FIG. 1 is a top view of an article that can be operated as a sandwich waveguide.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, light emitting diodes (LEDs), superluminescent LEDs (SLEDs), resonant cavity LEDs, sources of broadband light that is spectrally filtered such as with a monochromator, and so forth.

To "propagate" light through a region or structure is to transmit or otherwise cause the light to propagate through the region or structure. The light may be referred to as "propagated light" or "propagating light".

Propagating light can often be usefully characterized by direction of propagation, with direction typically illustrated by one or more rays. Where light changes direction in a way that can be illustrated as a vertex between an incoming ray and one outgoing ray, the change may be referred to as a "reflection"; similarly, to "reflect" light is to cause the light to change its direction of propagation approximately at a surface, referred to herein as a "reflection surface". Where light changes direction at a surface in a way that can be illustrated as a vertex between an incoming ray and two outgoing rays, one on each side of the surface, the change may be referred to as a "refraction", the surface may be referred to as a "refractive surface", and the two outgoing rays may be referred to as "transmitted" and "reflected", consistent with the above definition of reflection. The direction of a transmitted ray depends on the indices of refraction on the two sides of a refractive surface in accordance with well known relationships.

The term "waveguide", as used herein, refers to any combination of one or more components that operate to enable light of at least some energy range to propagate in some range of directions. Propagation of light enabled by a waveguide is sometimes referred to herein as "waveguiding". The term "propagation mode" is used herein to describe waveguiding in which light intensity is sufficiently stable or regular in its variation as a function of time that resulting light intensities can be described as a function of position within a waveguide; each propagation mode can therefore be specified by a respective intensity/position function.

One specific type of waveguide is a "sandwich waveguide", explained in greater detail below. The exemplary implementations described below address problems that arise in producing sandwich waveguides. Most currently known techniques to do so involve operations that are labor intensive and not suitable for mass production. Specifically, mechanical operations such as machining, milling, drilling, and polishing are typically required for each article that operates as a sandwich waveguide. For example, if the article includes glass parts, one of the parts is typically polished to produce a facet through which incident light is received. In addition, where a sandwich waveguide includes fluid, fabrication of fluidic components may also be required.

Articles that operate as sandwich waveguides can include various types of parts and components. As used herein, the term "body" is used with a meaning that relates to the related term "surface": As noted above, propagation of light can change at a surface, such as at a reflection surface or a refractive surface. A "body" is a part or component of material on which such surfaces can exist. The term "surface" can thereby refer to a simple surface such as an "approximately planar surface", meaning a surface area that approximates a plane; the term "surface", however, can also refer to a composite surface that includes a number of surface areas or portions of such areas, any of which can, in an appropriate context, be referred to as a "surface". In addition to being described by shape, surfaces, surface areas, or portions of such areas can be described by position or orientation. Also, surfaces, surface areas, or portions can be described by operation; for example, a "light interface" surface, area, or portion would operate as an interface between light on its two sides, such as a surface, area, or portion at which incident light is received or exiting light is coupled out.

A "light-transmissive" body, component, or part is made of material that allows light transmission through it; where an application requires light within a certain range of photon energies, the term "light-transmissive" refers to light transmission substantially throughout the application's range. A light-transmissive body or its parts may, for example, be "integrally formed" of light-transmissive material, meaning that the body or a larger body from which the body has been produced is a single piece of the light-transmissive material and does not include internal connections formed in some other way after the single piece was formed.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit.

To "photosense" is to sense photons, and to "photosense quantity" of photons is to obtain information indicating a quantity of the photons. The terms "photosensor" and "photosensing component" are used herein to refer generally to any element or combination of elements that senses photons, whether by photosensing quantity or any other information about the photons. A photosensor could, for example, provide an electrical signal or other signal that indicates results of sensing, such as a signal indicating quantity of incident photons.

In the implementations described herein, structures, systems, or parts or components of structures or articles may sometimes be referred to as "attached" to each other or to other structures, articles, parts, or components or visa versa, and operations are performed that "attach" structures, articles, or parts or components of structures or articles to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also integrally forming a body or a body's components or parts as described above and making other types of connections such as electrical connections between or among devices or components of circuitry. A combination of one or more parts connected in any way is sometimes referred to herein as a "structure".

A structure may be described by its operation, such as a "support structure" that can operate as a support; similarly, a "waveguide structure" includes parts or components that can operate as a waveguide. In addition, a structure may be characterized by the nature of its parts or the way in which they are connected; for example, a "layered structure" is a structure that includes one or more layers.

Within a structure or other article, components and parts may be referred to in a similar manner. One component of an article that includes a waveguide structure, for example, can be a "photosensing component" or simply "photosensor", as defined above; similarly, a "light source component" includes one or more light sources, which could provide light to a waveguide structure; an "optical component" performs an optical operation; an "electrical component" performs an electrical operation; a "fluidic component" performs a fluidic operation; a "light-transmissive component" transmits light; a "ducting component" performs ducting or operates as a duct; a "covering component" covers something, such as a part, component, or region; a "mounting surface" or "mounting area" is a surface or area on which something can be mounted; and other examples are defined further below. Other parts or components can be characterized by their structure.

Some of the components described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

An "integrated circuit" or "IC" is a structure with electrical components and connections produced by microfabrication or similar processes. Implementations of ICs described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An IC includes a "photosensor array" if the IC includes an array of cells, and at least some of the cells include respective photosensors.

In general, some of the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar process.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

Figure 2:
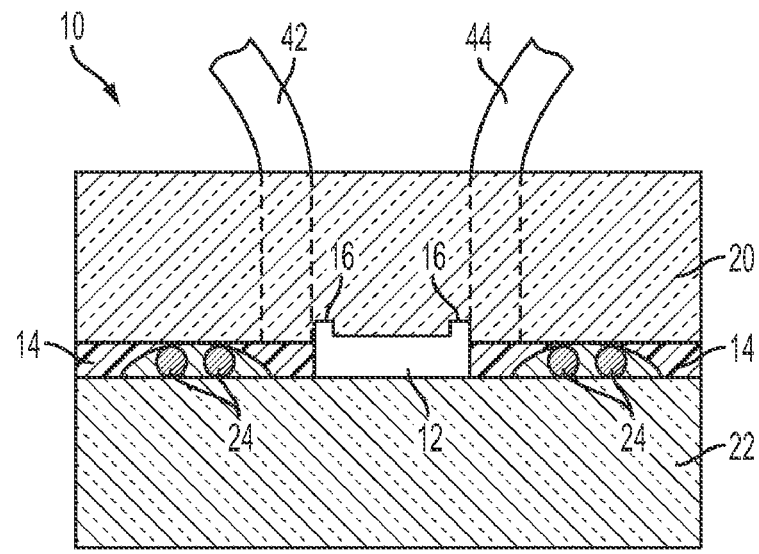
FIG. 2 is cross-sectional view taken along the line 2-2 in FIG. 1.
Figure 3:
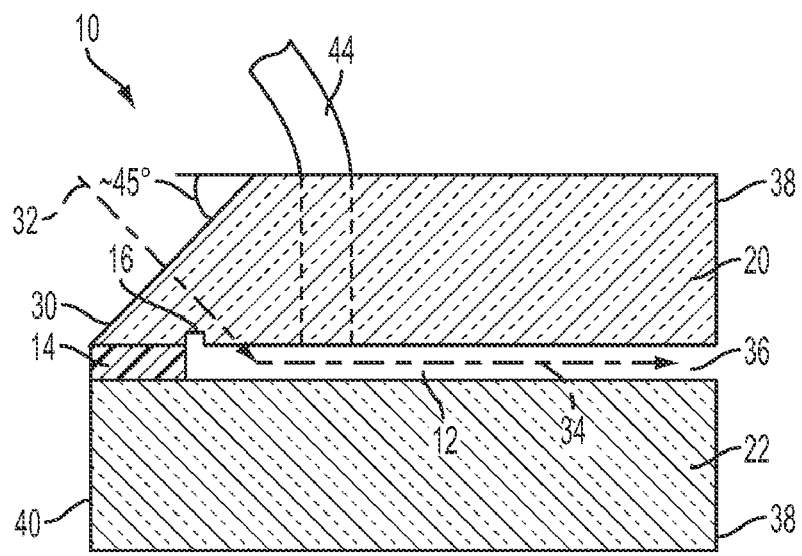
FIG. 3 is another cross-sectional view taken along the line 3-3 in FIG. 1.

FIGS. 1-3 illustrate an example of article 10 with components that can be operated as a "sandwich waveguide", meaning a waveguide in which two light-transmissive parts or components have facing surfaces that are approximately parallel and separated by a region with a lower refractive index than the light-transmissive components; the light-transmissive components could, for example, include glass or polymer material, and, for operation as a sandwich waveguide, the region between them could, for example, contain a liquid, gas, aerosol, or other fluid with a lower index of refraction; the term "fluid" is used herein to encompass liquids, gasses, and aerosols.

In principle, components could be operated as a sandwich waveguide without being connected, but components of article 10 are connected in such a way that article 10 includes a "sandwich waveguide structure", meaning a structure that can be operated as a sandwich waveguide. In addition, article 10 includes a "fluidic structure", used herein to refer to a structure that depends for its operation on fluid positioning or fluid flow, such as, for liquids or gases, in response to pressure or, for liquids, as a result of surface tension effects. The related term "channel" refers herein to any tube or other enclosed passage within a fluidic structure through which fluid flows during operation. A channel is therefore an example of a "fluidic region", used herein to refer to a region that can contain fluid. An operation "positions" fluid in a channel if it changes the fluid's position in any way that leaves the fluid in the channel.

An object "travels" within a channel or a portion of a channel or is caused "to travel" within a channel or a portion if the object moves through a succession of positions in the channel or portion. Similarly, light "emanates" from a channel or a portion of a channel if the light emanates from one or more objects within the channel or portion, where the term "object" is broadly understood to include even single molecules and small volumes of fluid from which light can emanate.

A channel or portion of a channel is treated herein as providing a directional orientation as follows: A "cross section" lies in a plane perpendicular to a direction in which a local net flow of fluid through the channel or portion can occur; a direction in which a cross section extends can be referred to as a "transverse direction" or a "lateral direction". "Longitudinal direction" is direction perpendicular to a cross section of a channel or portion; since longitudinal direction can differ for different cross sections, longitudinal direction may not be linear, but could include one or more curves or bends. Similarly, "length" of a channel or portion is measured in its longitudinal direction, and the term "lengthwise" similarly refers to motion or extent in a longitudinal direction of a channel or portion. Relative to a longitudinal direction, an "oblique direction" is a direction that is neither parallel to nor perpendicular to the longitudinal direction. A channel or portion with approximately uniform cross section and substantially linear longitudinal direction can be referred to as "straight", and the channels and portions described herein are generally straight unless otherwise indicated.

In order to contain fluid, a channel or other fluidic region is typically "bounded", meaning that surfaces or surface areas bound it on at least some sides. A "boundary" of a channel or portion is the surface or combination of surfaces within which fluid contained in the channel is confined. A "port" is an opening that extends through the boundary of a channel or portion such that fluid can enter or exit through the port; in general, a port is relatively small compared to the length of the channel or portion, and the boundary is treated as extending across the port as if the port did not exist. In a given cross section of a channel or portion it may therefore be "surrounded" along most of its boundary by material, meaning that more than half of its boundary in the cross section is bounded by material rather than being a port or ports.

FIG. 1 shows article 10 in a top view through one of the two light-transmissive components. In this view, the inner region between the light-transmissive components includes two main portions, channel portion 12 that can contain fluid and non-channel portion 14 that surrounds channel portion 12; channel portion is illustratively shaped like a "T", but could instead have an L-shape or any other suitable shape. Between portions 12 and 14 is groove 16, which can be more fully understood from FIGS. 2 and 3. Ports 18 are openings through one of the light-transmissive components, allowing entry and exit of fluid into and out of channel portion 12.

The cross section in FIG. 2 shows how light-transmissive components 20 and 22 are separated by spacers 24. As explained in greater detail below, components 20 and 22 can include acrylic, and non-channel portion 14 can be filled with epoxy material that seals a boundary around channel portion 12 and that also contains spacers 24, such as glass microspheres in suspension. In one implementation, channel portion 12 was 5 mm wide, but could have any suitable width.

The cross section in FIG. 3 further illustrates how light-transmissive component 20 has oblique surface 30, a light interface surface that is illustratively at an angle of approximately 45° to the inward-facing surfaces of components 20 and 22. As a result, incident excitation light at a direction approximately perpendicular to surface 30, as illustrated by arrow 32, can cause and couple with light propagating through channel portion 12, as illustrated by arrow 34 (FIG. 4, described below, illustrates more accurately how light would propagate through channel portion 12). Article 10 therefore includes a sandwich waveguide structure as defined above. Alternatively, light propagating in such a waveguide can also couple out of the waveguide through an interface surface such as surface 30.

In the illustrated implementation, the end of channel portion 12 at right in FIG. 3 is open, providing an additional port 36 through which fluid can enter into or exit out of channel portion 12. Alternatively, article 10, instead of ending at transverse end surface 38, could extend to another area with ports similar to ports 18, such as with a part symmetrical about the position of surface 38; in this case, fluid could flow through channel portion 12 between ports 18 and similar ports at the opposite end of channel portion 12.

Articles similar to article 10 in FIGS. 1-3 have been successfully fabricated with a process described below, using light-transmissive components 20 and 22 made from acrylic and ultraviolet (UV) curable epoxy injected into non-channel portion 14. Schmidt, O., Bassler, M., Kiesel, P., Knollenberg, C., and Johnson, N., "Fluorescence Spectrometer-on-a-fluidic-chip", Lab on a Chip, 2007, DOI: 10.1039/b618879f, incorporated herein by reference, describes results obtained with such an implementation. The process is not, however, well-suited for mass production, in part because it is labor-intensive.

The process can begin by cutting equal area pieces of a large acrylic sheet with a laser cutter, with one piece being for light-transmissive component 20 and another being for light-transmissive component 22. In one implementation, a 1.5 mm thick acrylic sheet was used, and each light-transmissive component was a rectangle measuring 25 mm×75 mm. Treating light-transmissive component 22 as a substrate, a mirror can then be evaporated onto its lower or upper surface, the surface that will be disposed away from or towards component 20. Light-transmissive component 20 can be polished to produce oblique surface 30 of optical quality and with an appropriate angle for incident light, i.e. an angle at which incident light can couple with light propagating within channel portion 12. As with component 22, mirrors can be evaporated, such as on end surfaces 38 and 40, to provide a form of light recycling within channel portion 12. Techniques that employ mirrors are described in greater detail in co-pending U.S. patent application Ser. No. 11/777,976, entitled "A Method and Apparatus for Improved Light Distribution in an Anti-Resonant Waveguide Sensor" and incorporated herein in its entirety. Also, 50 μm deep groove 16 can be formed in the lower surface of component 20 or upper surface of component 22, and ports 18 can also be formed, all using a laser cutter or drill.

When components 20 and 22 are fully prepared, spacers 24 can be positioned on the upper surface of component 22, i.e. the surface that will be disposed toward the lower surface of component 20. In one successful implementation, each spacer 24 was a glass microsphere with a diameter of 100 μm and spacers were positioned by depositing drops of UV curable epoxy that included spacers. Then, component 20 was positioned in alignment with component 22 and mounted on it to form a sandwich structure in which spacers 24 defined a distance between components 20 and 22, the distance that also serves as the height of channel portion 12. UV light was then applied to cure the epoxy in which spacers 24 were deposited.

Non-channel portion 14 can then be filled with UV curable epoxy to seal channel portion 12 so that fluid is held within it. This has been successfully accomplished by using capillary force suction to inject pure, low viscosity UV curable epoxy into non-channel portion 14 from the side of the sandwich structure with spacers. Epoxy injected in this manner stops flowing when it reaches groove 16. Then, UV light can be applied to cure the epoxy in non-channel portion 14.

Rather than using spacers and injected epoxy, an appropriate polymer material such as SU-8 could be deposited on the upper surface of component 22 and photolithographically removed from channel portion 12. In this alternative implementation, the polymer layer portion remaining after photolithography would seal channel portion 12 and would also determine distance between components 20 and 22. Similarly, a double-sided tape can be used such as 501FL or 9461P tape from 3M Company. Channel portion 12 can be cut out of the tape with a laser cutter before the tape is applied to surfaces of components 20 and 22.

After producing a structure as described above, additional operations can be performed to attach fluidic components such as tubing 42 and 44 (FIGS. 2 and 3) and also optical and electrical components. For example, such operations could attach one or more light sources and one or more photosensing components that, for example, include optical fibers and spectrometers or include one or more ICs positioned along channel portion 12, such as with techniques described in U.S. patent application Ser. No. 11/316,660, entitled "Providing Light to Channels or Portions", and incorporated herein by reference, or receiving emanating light through an imaging component such as a lens.

In exemplary implementations, a cross section of channel portion 12 can be 3 mm wide and as high as the distance between components 20 and 22, which can be determined by the diameter of spacers 24. Rather than 100 μm spacers as mentioned above, spacers of other diameters could be used, such as 25 μm. Various other thicknesses of acrylic could be used for components 20 and 22, such as 1.0 mm.

Article 10 in FIGS. 1-3 provides an initial example of an article, structure, or component that is "structured to operate as a sandwich waveguide", an expression that is used herein to refer to a combination of structural features that allow sandwich waveguide operation. Such an article, structure, component, or part is sometimes treated herein as providing a directional orientation as follows: Facing surfaces that are approximately parallel are referred to as "inward surfaces", while surfaces that face away from the region between the inward surfaces are referred to as "outward surfaces".

Figure 4:
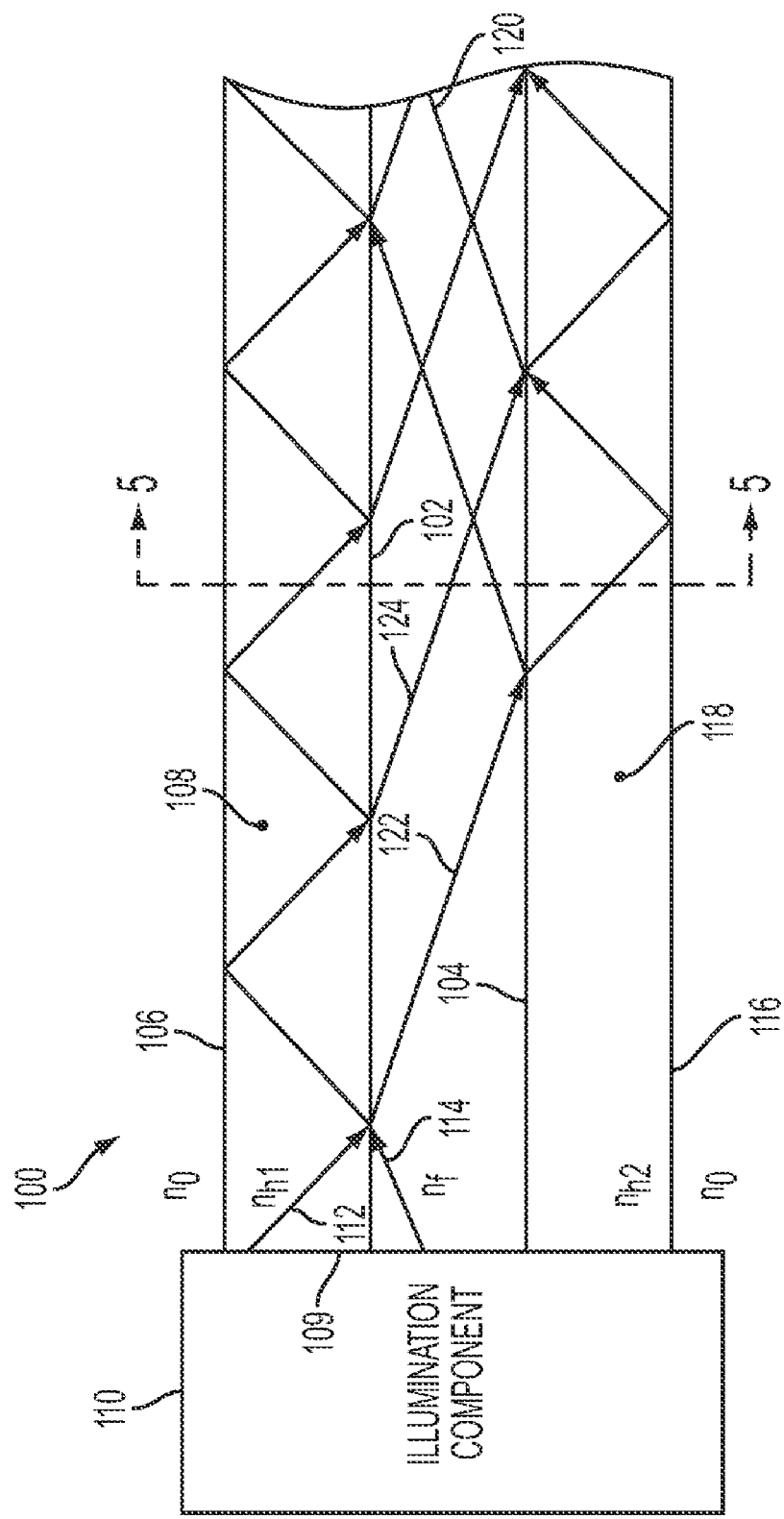
FIG. 4 is a schematic diagram showing how light can propagate through a sandwich waveguide.

FIG. 4 illustrates schematically one example of how light can propagate through a sandwich waveguide such as that provided by article 10 in response to incident light similar to that represented by arrow 32 in FIG. 3. In FIG. 4, waveguide 100 illustratively includes four surfaces between regions of different refractive indices. Inner surfaces 102 and 104 are on either side of a channel that can contain fluid, with a refractive index of $n_f$; the fluid can carry analytes or objects through the channel as described in U.S. patent application Ser. No. 11/316,660, entitled "Providing Light to Channels or Portions" and incorporated herein by reference. Outer surface 106 is at the opposite side of light-transmissive component 108 with a refractive index $n_{n1} > n_f$. Incident surface 109 is illustratively a light interface surface that receives incident light from illumination component 110, such as in one of the ways illustrated by arrows 112 and 114. Outer surface 116 is on the opposite side of light-transmissive component 118 with refractive index $n_{h2} > n_f$.

Regions outside surfaces 106 and 116 can be filled, for example, with air or another substance with a refractive index $n_0 < n_f$. As a result, virtually all incident light from component 110 is confined between outer surfaces 106 and 116 due to total internal reflection (TIR), and one of a number of possible propagation modes can be excited in which the majority of light intensity is in the channel between surfaces 102 and 104. This is suggested schematically by rays 120, 122, and 124 which propagate within channel portion 12.

Various examples of propagation modes referred to as "anti-resonant waveguide modes" are described in Kiesel, et al., U.S. Patent Application Publication No. 2006/0092413; U.S. patent application Ser. No. 11/316,660, entitled "Providing Light to Channels or Portions"; and U.S. patent application Ser. No. 11/315,797, entitled "Fluorescent Reader Based on Anti-Resonant Waveguide Excitation", all of which are incorporated herein by reference in their entireties. Various other terms have been used to describe similar propagation modes, as exemplified by Goddard, N. J., Singh, K., Bounaira, F., Holmes, R. J., Baldock, S. J., Pickering, L. W., Fielden, P. R., and Snook, R. D., "Anti-Resonant Reflecting. Optical Waveguides (ARROWs) as Optimal Optical Detectors for MicroTAS Applications", dias.umist.ac.uk/NJG/Abstracts/MicroTAS/MicroTas2.htm, pp. 1-5; Singh, K., and Goddard, N. J., "Leaky Arrow Waveguides for Optical Chemical and Biosensors", (Abstract Submitted to Biosensors 1998), dias.umist.ac.uk/NJG/Abstracts/Biosensors/AR-ROW-Biosensors.htm, pp. 1-2; and Singh, K., Liu, C., Capjack, C., Rozmus, W., and Backhouse, C. J., "Analysis of Cellular Structure by Light Scattering Measurements in a New Cytometer Design Based on a Liquid-Core Waveguide", IEE Proc.-Nanobiotechnol., Vol. 151, No. 1, February 2004, pp. 10-16, all of which are incorporated herein by reference. In addition, further propagation modes that can be excited in sandwich waveguides are likely to be discovered, and it is contemplated that the techniques described herein can be used with any sandwich waveguide structure in which such propagation modes can occur.

Figure 5:
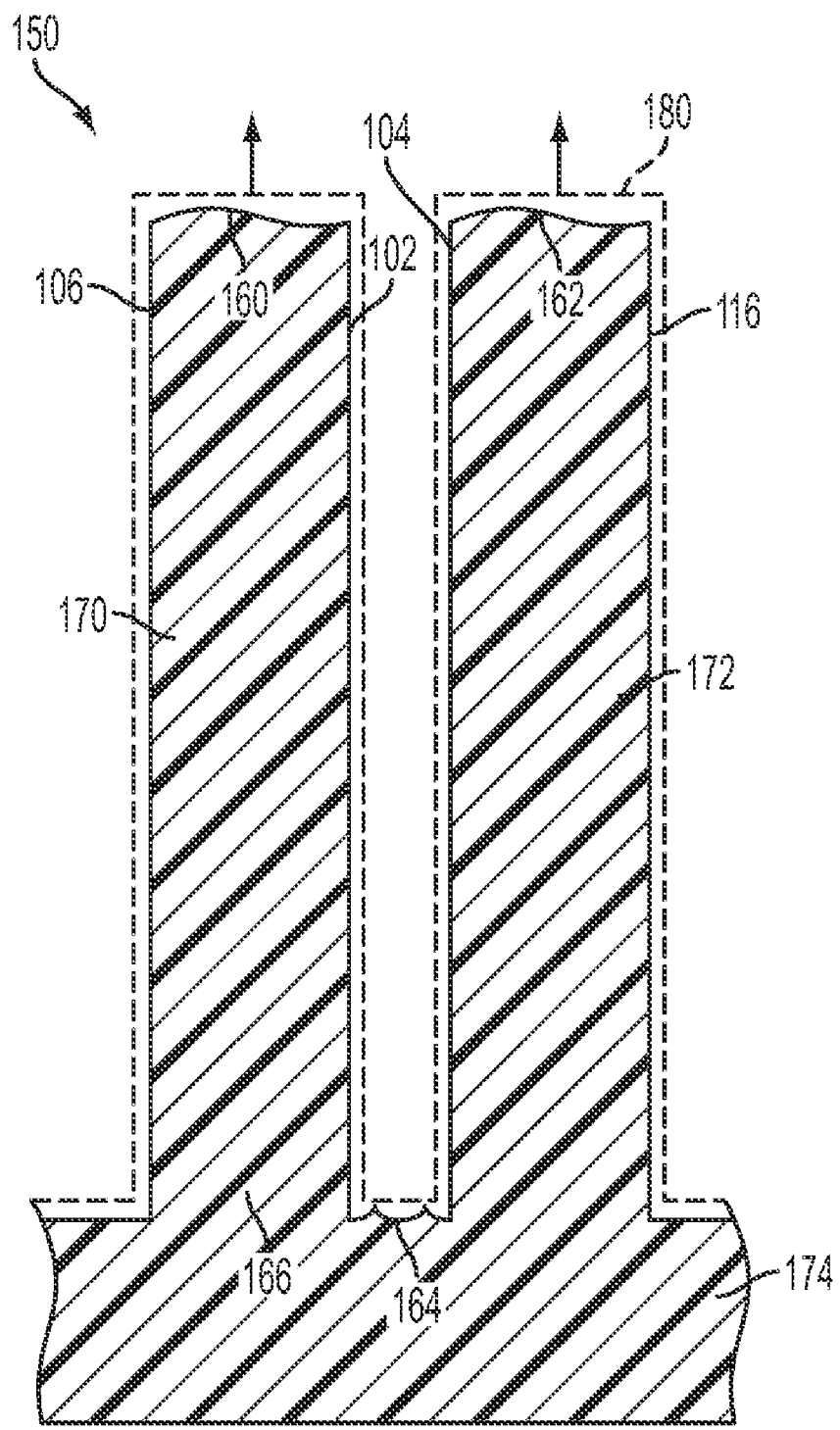
FIG. 5 is a cross-sectional view of an article that can be operated as a sandwich waveguide, illustratively along the line 5-5 in FIG. 4.

FIG. 5 illustrates features of article 150, which includes surfaces 102, 104, 106, and 116 that can be operated as a sandwich waveguide in the manner described in relation to FIG. 4. Although the features in FIG. 4 are general, and have also been implemented as in article 10 (FIGS. 1-3), the implementation in FIG. 5 is illustratively taken along a line similar to line 5-5 in FIG. 4, and the surfaces in FIG. 5 are therefore labeled with the same reference numerals as in FIG. 4. FIG. 5 also illustrates, however, additional features that result from "complementary surface fabrication processes", an expression used herein to refer to any of various techniques in which contact between non-solid material and a solid structure or component produces a surface that has a complementary shape to that of the solid structure or component; the surface of the solid structure or component is sometimes referred herein as a "complementary solid surface". An example of a complementary solid surface is illustrated by dashed line 180 in FIG. 5, with the upward arrows indicating a direction of sliding, one of the possible ways complementary solid surfaces could be removed during complementary surface fabrication processes. Examples of such processes include various types of molding, casting, and embossing, including injection molding and hot embossing.

Article 150 includes several "complementary surface artifacts", meaning any detectable characteristic or feature of a structure that results from use of a complementary surface fabrication process to produce it. Some of the complementary surface artifacts are "exposed artifacts", meaning that they are at an exposed surface of article 150. Other artifacts, however, are "sub-surface artifacts", meaning that they are present beneath the surface of article 150.

Artifacts 160, 162, and 164 are examples of exposed artifacts. Each of these artifacts results from contact and then separation between a complementary solid surface, such as a mold or embossing plate, and non-solid material. These artifacts can arise for various reasons, such as adhesion between the complementary solid surface and the non-solid material, because of slight suction-related effects, or because of trapped air.

In contrast to artifacts 160, 162, and 164 resulting from separation, surfaces 102, 104, 106, and 116 are examples of exposed complementary surface artifacts that result from a smooth complementary solid surface and good filling or contact of non-solid material against the complementary solid surface. More specifically, it is well known that optical quality surfaces can be produced by complementary surface fabrication processes such as injection molding and hot embossing in which a smooth complementary solid surface contacts an appropriate non-solid material, and optical quality surfaces produced in this manner are further examples of complementary surface artifacts. The term "optical quality surface", as used herein, refers to a surface of a light-transmissive component that satisfies a smoothness criterion appropriate to a given application; in other words, an optical quality surface must be sufficiently smooth that reflection and transmission at the surface is sufficient for the application, or, conversely, it must not be so rough as to preclude such reflection and transmission due to strong light scattering at the rough surface. An optical quality surface, surface area, or portion is sometimes referred to herein as having "optical quality". An application's required efficiency of reflection and transmission can, for example, be specified by a maximum feature size that indicates that the roughness or size of features on a surface is smaller than the maximum feature size. Sometimes this maximum feature size is specified as $\lambda/n$, where $\lambda$ is the smallest wavelength used in the application and n is a positive number such as 20 or 100, with a higher number indicating greater optical quality.

Joints 166, in contrast, are examples of sub-surface artifacts. As a result of complementary solid surface fabrication, each of wall-like parts 170 and 172 is integrally joined to base part 174 with no discontinuity of material. Although sub-surface artifacts may not be externally visible, they can often be detected by cutting or otherwise opening a solid part.

The examples illustrated in FIG. 5 are merely a few of the many types of complementary surface artifacts that can arise. Various additional features of the complementary solid surface, including its shape, its dimensions, and its surface texture, can all leave exposed artifacts in an article produced with complementary surface fabrication; for example, wall-like parts that all have substantially equal heights as in FIG. 5 could be artifacts of a complementary solid surface that has equally deep recesses in which the wall-like parts are formed. Also, the injection point of an injection mold and a similar overflow point at which excess injected material can exit the mold can each leave an exposed artifact. Sub-surface artifacts, on the other hand, often result from characteristics of the non-solid material, and can be preserved by subsequent operations that harden it.

Article 150 in FIG. 5 illustrates an example of a body with parts that are integrally formed of light-transmissive material, as described above, and it is also structured to operate as a sandwich waveguide, as explained in greater detail below in relation to exemplary implementations. Article 150 and similar articles described below are sometimes treated herein as providing a directional orientation as follows: Base part 174 is "under" or "below" wall-like parts 170 and 172, which are examples of "wall parts" that extend "up" or "upward" from a "base", in this case base part 174, and therefore each has a "height" that can be measured from the base. Each of wall-like parts 170 and 172 can further be described as having a region connected to a connecting part such as base part 174 and another region disposed away from base part 174.

Because the inward surfaces of the wall parts are substantially parallel they do not meet each other, but instead meet a "base area", meaning a surface area that extends between the lower ends of the inward surfaces; in general, the base area can have any appropriate shape, and its shape provides another example of a complementary surface artifact. The base area extends between two lateral borders at which the inward surfaces meet it, and each of the inward surfaces in FIG. 5 is illustratively approximately planar and also approximately perpendicular to the base area.

In the illustrated example, the upper edges of the inward surfaces are "open", meaning that the wall parts do not connect or otherwise meet above the inward surfaces. A part that is on or over the upper ends of the wall parts is also sometimes referred to herein as being "over" or "above" the inward surfaces and the base area, and may be referred to as a "cover part"; if a cover part is connected to a structure, part, or component that includes the wall parts, it may be referred to as "connected over" the wall parts. A cover part's lower surface, together with the base area and the two inward surfaces or areas, can bound or surround a fluidic region "along a length", meaning that, if the fluidic region were functioning as a channel, a length of the channel would be bounded in all transverse directions even if open at its longitudinal ends; without the cover part, the fluidic region would be "partially bounded" along a length, because it would be bounded by the base area and the two inward surfaces or areas along the length but would not be bounded between the open edges of the inward surfaces or areas.

Figure 6:
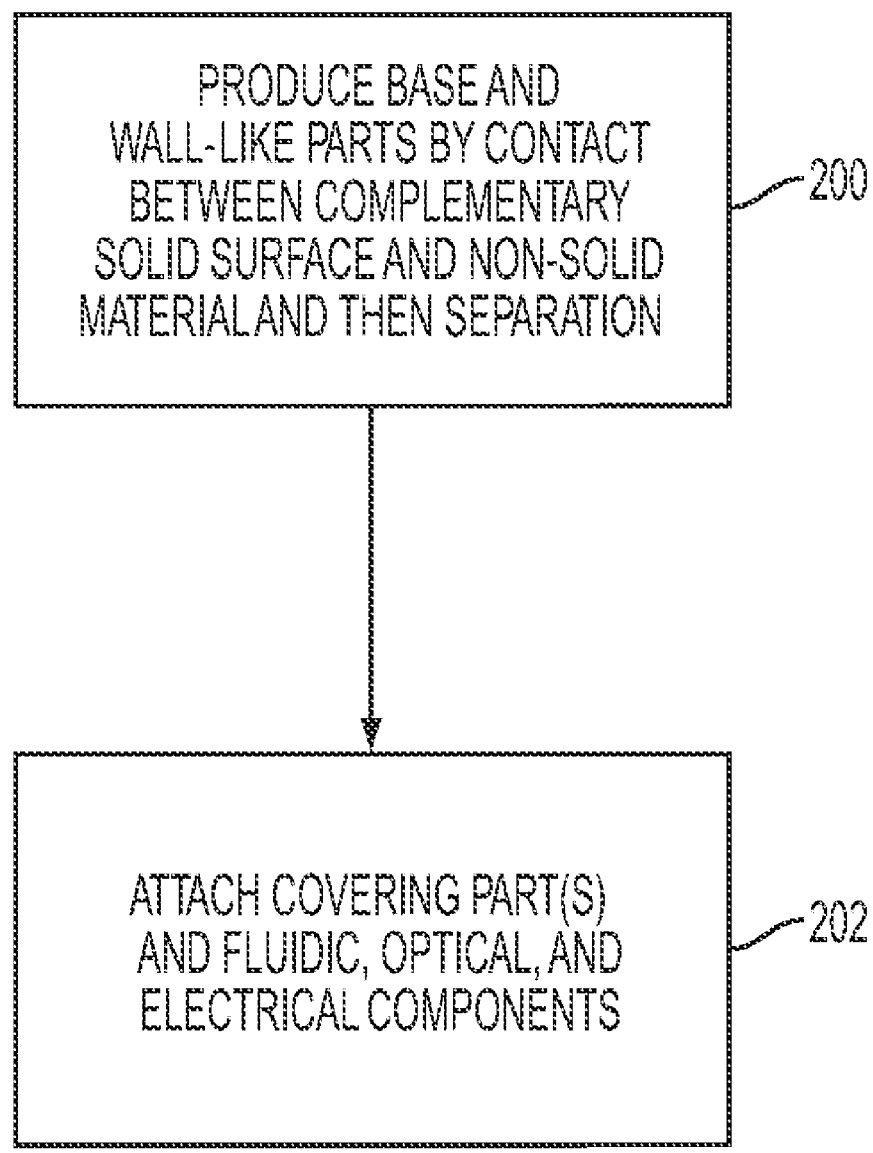
FIG. 6 is a flowchart showing stages in producing a fluidic structure using components such as the article of FIG. 5.

FIG. 6 illustrates how operations to produce a fluidic structure using components like article 150 in FIG. 5 can be divided into two stages. In the stage shown in box 200, base part 174 and wall-like parts 170 and 172 are produced by contact between a complementary solid surface and a suitable non-solid material and then separation, leaving the non-solid material with the complementary shape. The stage in box 200 could also include operations to harden the non-solid material, and might also include some incidental processing, such as to machine inlets, outlets, wiring openings, and so forth. Then, in a second stage shown in box 202, various other parts and components are attached, such as a covering part over the channel between parts 170 and 172; other fluidic components such as tubes, and so forth; and other optical and electrical components, such as light sources and photosensing components. The covering part can, for example, be a cover slide or other part of acrylic or glass; to connect it over the channel, epoxy can be applied to the top sides or surfaces of wall-like parts 170 and 172, and the cover slide can then be aligned so that the epoxy holds it in an appropriate position.

The operations in box 200 in FIG. 6 allow mass production of components similar to article 150 in FIG. 5. For example, a number of components could be produced on a wafer or on a sheet of acrylic or other such support structure, and the wafer or sheet could then be diced. Also, as can be understood from the exemplary implementation in FIG. 7, described below, no additional polishing is necessary to produce an oblique surface to receive incident light from a light source, and no additional drilling is necessary to form inlet and outlet ports because channels can have inlets and outlets at their open ends. In addition, the operations in boxes 200 and 202 can be implemented to produce sandwich waveguide structures with simple and cheap manufacturing techniques. Also, additional operations could be performed, such as to somehow deposit mirrors on walls to recycle light.

In the techniques of FIGS. 5 and 6, base part 174 operates similarly to a substrate, so that, compared to article 10 in FIGS. 1-3, resulting article 150 can be characterized as rotated by 90° with respect to the substrate. It is believed, however, that complementary surface fabrication processes can be used with other configurations in which this would not be the case.

The operations in box 200 could be implemented with a "single step" of complementary surface fabrication, creating multiple channels bounded by optical surfaces in a single run. In other words, the single step would create uncovered fluidic structures and would also create both optical quality surfaces for waveguiding and also optical quality surfaces for Coupling incident light.

The technique in FIG. 6 could be implemented in many different ways. Possible dimensions would include channel wall thicknesses of approximately 200 µm, wall heights of approximately 1 mm, and spacing between inner channel surfaces of approximately 100 µm, resulting in a channel cross section of approximately 1 mm×100 µm. In general, walls such as wall-like parts 170 and 172 can be made as thin as necessary to achieve a desired level of light confinement in fluid in a channel between the walls.

If injection molding is used to produce article 150, the non-solid material could include any appropriate polymer material such as acetal, nylon, polypropylene, polycarbonate, acrylonitrile butadiene styrene (ABS), polybutylene, polystyrene, or acrylic. Similarly, if the process is hot embossing, the non-solid material could include any appropriate polymer material such as polymethyl methacrylate (PMMA), polycarbonate, polyether imide (PEI), polytetrafluoroethylene (PTFE/Teflon®), and polyetheretherketone (PEEK). To improve properties of a polymer for use in a complementary surface fabrication process, additives such as glass fiber, carbon fiber, and various other such materials could be added.

Kalveram, S., and Neyer, A., "Precision moulding techniques for optical waveguide devices", SPIE, Vol. 3135, 1997, pp. 2-11, incorporated herein by reference, describe how other types of waveguides could be produced using injection molding and hot embossing. Based on the teachings herein, one of skill in the art could also make use of techniques similar to those of Kalveram and Neyer in implementing techniques to produce sandwich waveguides as described herein. Also, molds or plates for injection molding, hot embossing, or other complementary surface fabrication processes could be produced with laser cutting, milling, photolithography-based etching, or another similar operation.

Figure 7:
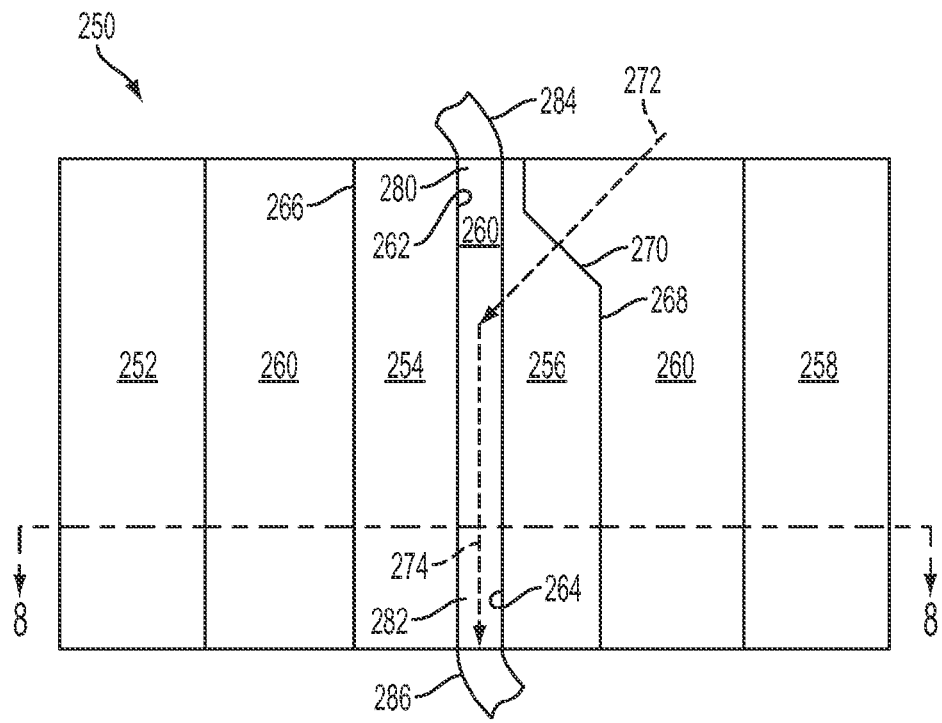
FIG. 7 is a top view of an article that can be implemented with techniques illustrated in FIGS. 4-6.
Figure 8:
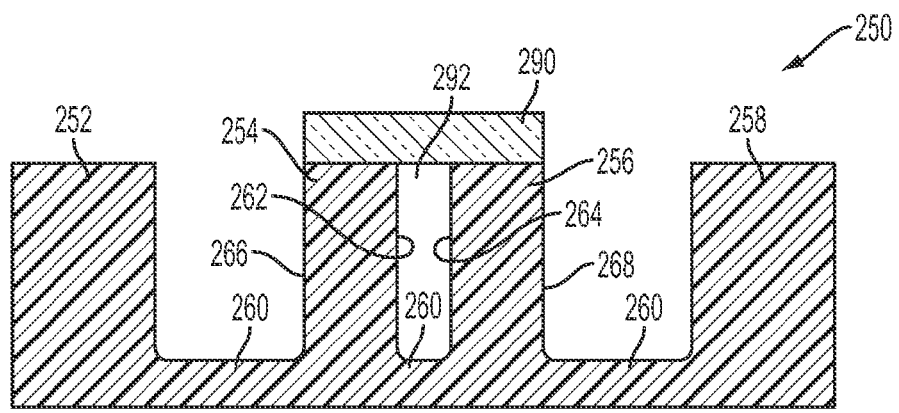
FIG. 8 is a cross-sectional view taken along the line 8-8 in FIG. 7.

FIGS. 7 and 8 illustrate an implementation of the techniques described above in relation to FIGS. 4-6. FIG. 7 shows a top view of article 250, while FIG. 8 shows a cross-sectional view of article 250 taken along the line 8-8 in FIG. 7.

As shown in FIG. 7, walls 252, 254, 256, and 258 are separated by spaces in which base 260 is visible. Inner surfaces 262 and 264 of walls 254 and 256 are counterparts of surfaces 102 and 104 in FIGS. 4 and 5, while outer surfaces 266 and 268 are counterparts of surfaces 106 and 116. Oblique surface 270 is a light interface surface that can receive excitation light as indicated by arrow 272, and therefore, operates similarly to oblique surface 30 (FIG. 3); the excitation light can then cause and couple with light propagating in a channel between surfaces 262 and 264, as indicated by arrow 274. Although surface 270 is not parallel to any of surfaces 262, 264, 266, and 268, all of these surfaces are approximately perpendicular to a plane, illustratively any plane parallel to the plane in which a surface of base 260 lies; it would also be possible, however, for all of surfaces 262, 264, 266, 268, and 270 to be approximately perpendicular to another plane, such as a plane at an oblique angle to a surface of base 260, and it would similarly be possible for walls 252, 254, 256, and 258 to have different heights rather than being of equal height.

The channel between surfaces 262 and 264 can have a port at each end, with port 280 being an inlet port and port 282 being an outlet port in one implementation. As shown, tubing parts 284 and 286 can be attached to ports 280 and 282, respectively; this illustrates how inlets, outlets, and tubing can be attached to article 250 parallel to base 260, an approach that can achieve more robust connections. Alternatively, inlets and outlets can be provided in walls 254 or 256 similarly to ports 18 (FIGS. 1-3) and also connected to tubing parallel to base 260, which would also achieve more robust connections as described above.

In addition to the features described above, the cross section in FIG. 8 shows cover slide 290, a covering part or component that is connected over and encloses channel 292 between walls 254 and 256 with its lower surface meeting and extending between surfaces 262 and 264, but does not extend over the spacing between walls 252 and 254 or the spacing between walls 256 and 258, which, as a result, are left open. Cover slide 290 is illustratively mounted on the upper surfaces or areas of walls 252 and 254, which serve as mounting surfaces or areas and which can be approximately planar. Cover slide 290 can, for example, be made of acrylic or any other appropriate material, and can have any appropriate optical properties: For example, to block environmental light, cover slide 290 could be black; for other purposes, it could be reflective or transparent.

Figure 9:
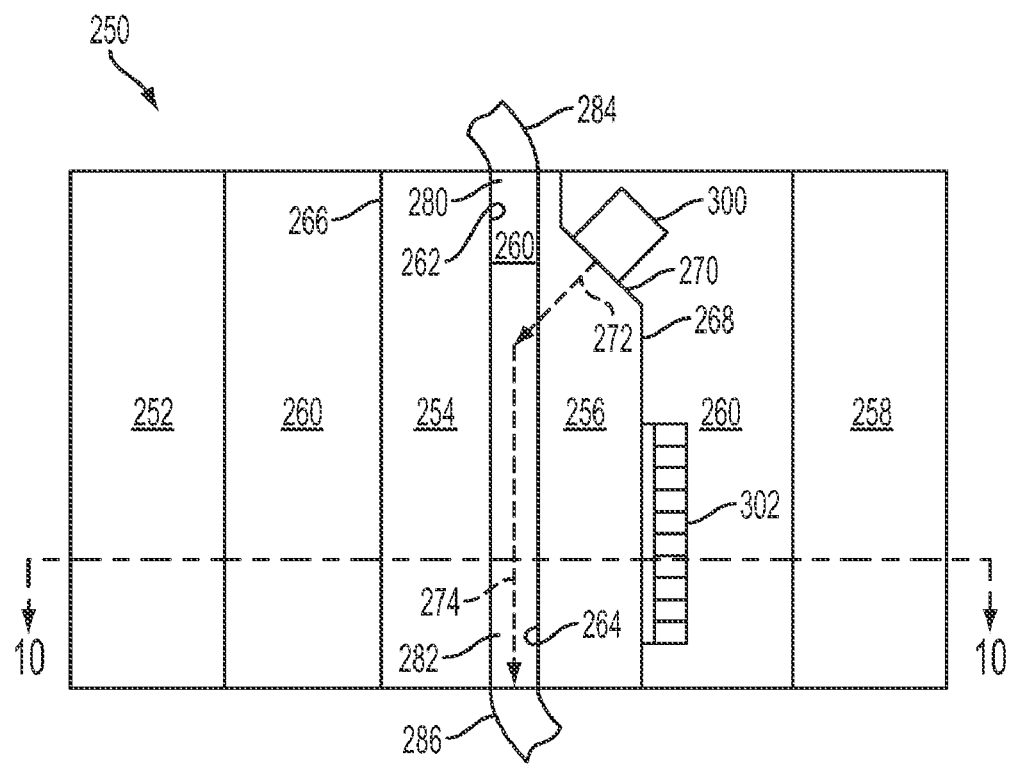
FIG. 9 is a top view of another article that can be produced with techniques as in FIGS. 4-6.
Figure 10:
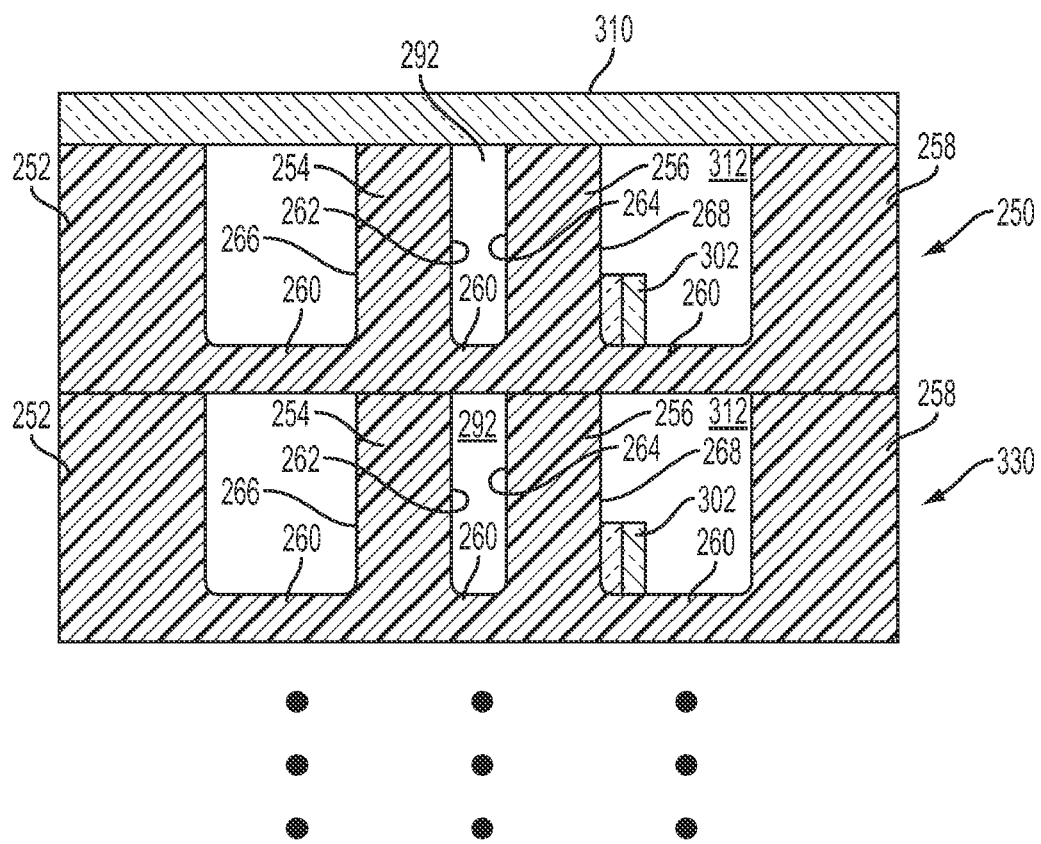
FIG. 10 is a cross section taken along the line 10-10 in FIG. 9.

FIGS. 9 and 10 illustrate an alternative implementation in which article 250, with parts having the same reference numerals as in FIGS. 7 and 8, supports light source 300 adjacent oblique surface 270, and also supports photosensing component 302 along outer surface 268. Alternatively, some applications could be implemented with one or more light sources attached to outer surface 268 and with one or more photosensing components attached to light interface surface 270.

Light source 300 can, for example, be any suitable component, such as a laser diode or other narrow band light source. Photosensing component 302 can similarly be implemented with any appropriate component, but it is believed that one or more ICs positioned along surface 268 in the manner described in U.S. patent application Ser. No. 11/316,660, entitled "Providing Light to Channels or Portions" and incorporated herein by reference, would be especially suitable. In such an implementation, the relative dimensions would depart somewhat from those illustrated in FIGS. 9 and 10: For example, wall 256 could be 200 μm thick and 1 mm high as noted above, while an unpackaged detector array could have a depth of about 100 μm and a cell size of 50 μm, and could easily be accommodated between walls 256 and 258, even if mounted on spacers and having a number of rows of cells along the height of wall 256; a packaged array, on the other hand, would be much deeper, possibly requiring a larger spacing between walls 256 and 258 to accommodate the package.

The cross section in FIG. 10, taken along the line 10-10 in FIG. 9, also shows how cover slide 310, attached to the upper surfaces or areas of walls 252, 254, 256, and 258 which serve as mounting surfaces or areas, can extend over spacing 312 between walls 252 and 254 and the spacing between walls 256 and 258. As a result, cover slide 310 covers spacing 312 containing light source 300 and photosensing component 302, providing a nicely packaged system. In addition, if cover slide 310 is black or reflective as described above in relation to FIG. 8, it can also block environmental light that could otherwise enter through surfaces 266 and 268. As can also be seen in FIG. 10, photosensing component 302 (and also light source 300) can be securely attached where wall 256 meets base 260, providing a more robust connection than in the middle of a flat surface. Any appropriate attachment or mounting technique can be used, and the implementation in FIGS. 9 and 10 could be readily modified to accommodate multiple light sources and multiple photosensing components.

FIG. 10 also illustrates how base 260 of article 250 can act as the covering part of article 330, illustratively implemented in the same way as article 250, with its parts having the same reference numerals. Base 260 is similarly attached to the upper surfaces or areas of walls 252, 254, 256, and 258 of article 330, so that the upper surfaces or areas serve as mounting surfaces or areas, Furthermore, as suggested by the downward ellipses in FIG. 10, a stack of identical components could be extended until a desired size or a practical limit.

Figure 11:
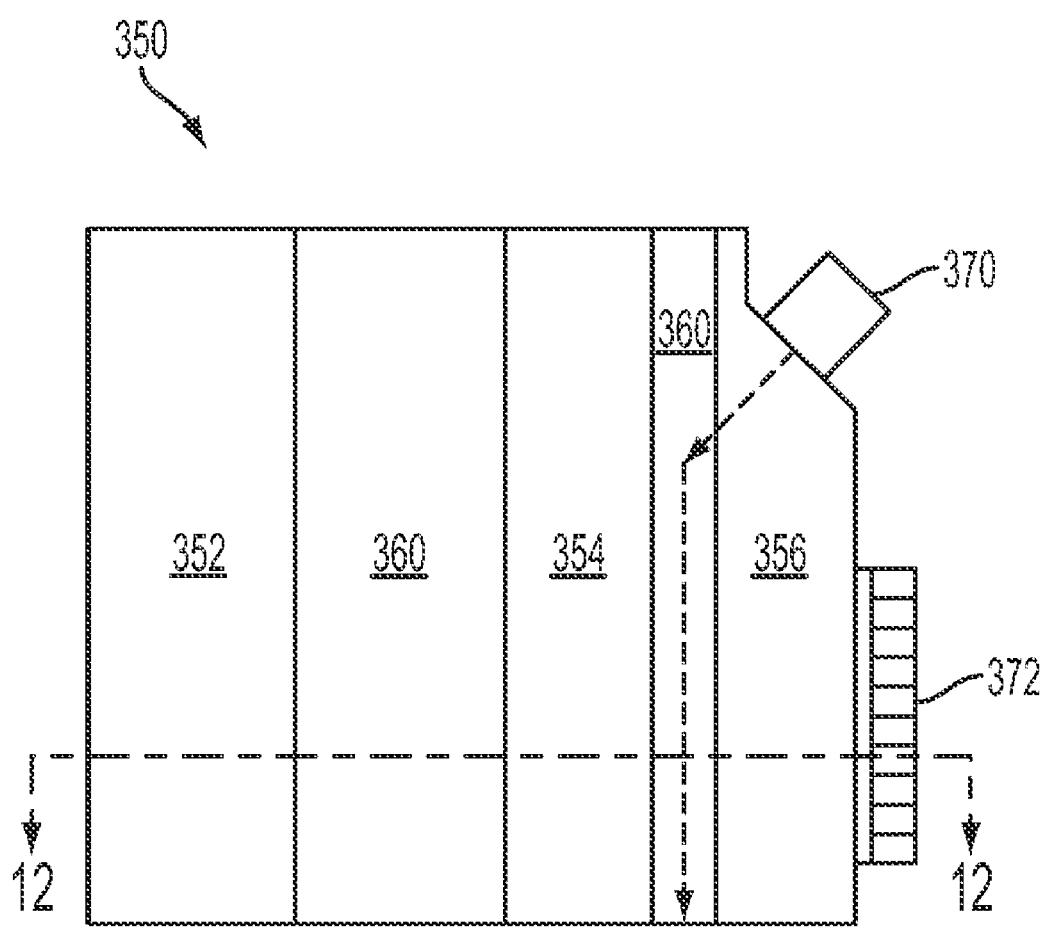
FIG. 11 is a top view of a stack of articles that can be produced with techniques as in FIGS. 4-6.
Figure 12:
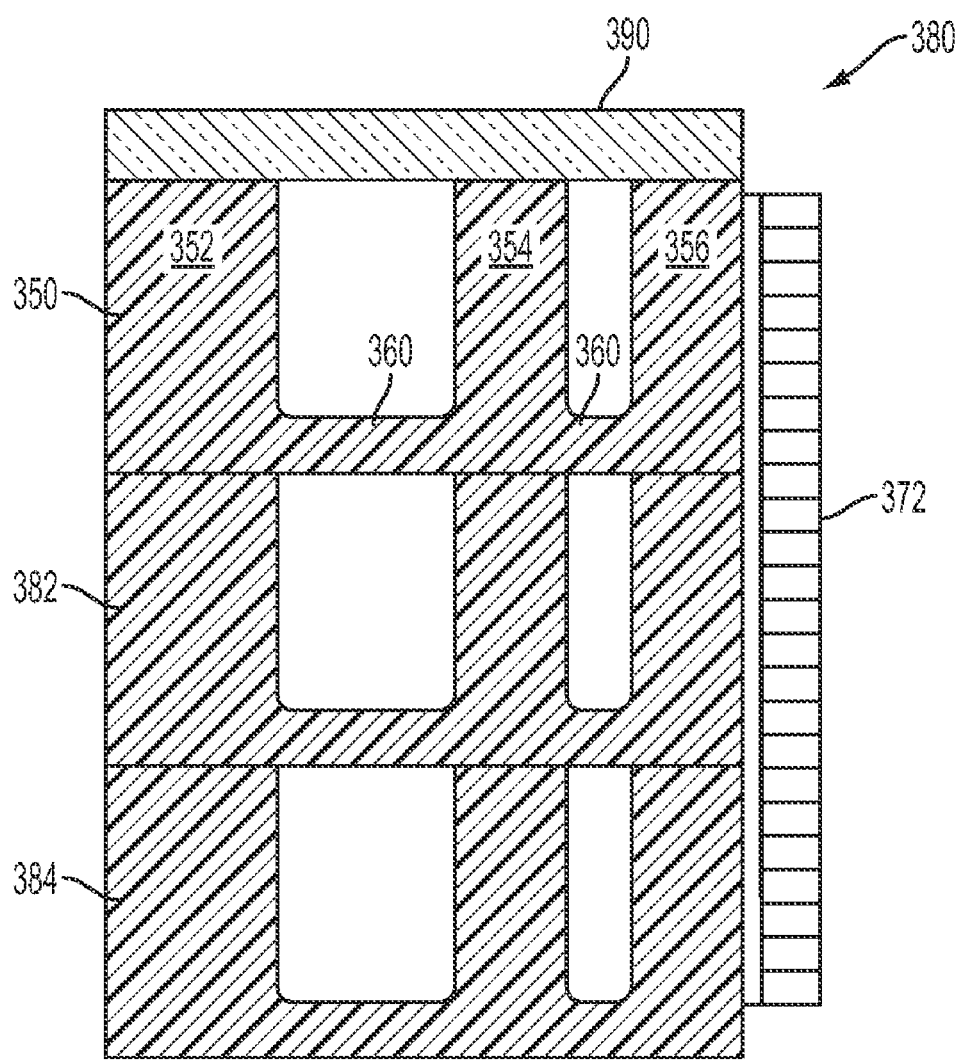
FIG. 12 is a cross-sectional view of the stack of FIG. 11, taken along the line 12-12.

FIGS. 11 and 12 illustrate yet another variation in which each article has features as illustrated in the top view of FIG. 11, and the articles are stacked as illustrated in the cross section of FIG. 12. As a result, a single photosensing component, such as an IC with a two-dimensional array of photosensors, can be attached to the stacked articles.

In FIG. 11, article 350 has walls 352, 354, and 356, counterparts respectively of walls 252, 254, and 256 in FIGS. 7-10. Base 360, however, has been cut adjacent to wall 356, so that the outer surface of wall 356 is at the perimeter of article 350. As in FIG. 9, light source 370 and photosensing component 372 are attached to wall 356, but are not under a covering part such as a slide.

FIG. 12 shows a cross section of stack 380 that includes article 350 and also similar articles 382 and 384 Although article 350 is covered by cover slide 390, its base 360 covers article 382, and the base of article 382 in turn covers article 384, in each case by attachment to mounting surfaces or areas on walls as described above. The outward surfaces of wall 356 and the walls below it are aligned to form a side mounting surface on stack 380. In this implementation, photosensing component 372 is attached to the side mounting surface and extends along the channels of all three of articles 350, 382, and 384, significantly reducing the number of required electrical connections to photosensing components. Similarly, light source 370 could be implemented as an array of light sources all attached to oblique surfaces of articles 350, 382, and 384, further reducing the required number of electrical connections.

The implementations in FIGS. 1-12 illustrate various sandwich waveguide techniques that are especially suitable for anti-resonant waveguiding; anti-resonant waveguiding is an excellent technique to guide light, such as in a low refractive index fluid bounded by high refractive index components. Anti-resonant waveguiding is therefore useful in optical analysis of fluids or objects traveling in fluids, such as in fluidic structures used in obtaining information about fluorescence of analytes. The techniques could be readily extended to other waveguiding techniques that obtain information about other optical characteristics of fluids and objects that travel in fluid. More generally, the techniques have great potential for integration of optical sensing techniques into lab-on-a-chip devices, such as disposable lab-on-a-chip systems that require light guiding in liquids.

The fabrication techniques described above in relation to FIGS. 4-12 can be implemented simply and cheaply to fabricate very robust fluidic structures. For example, they can be implemented without operations that polish glass slides or acrylic sheets; they can be implemented without spacer beads or other spacer materials to provide accurate spacing between glass slides or acrylic sheets; and they can be implemented without complicated channel sealing operations. The exemplary implementations described above allow single step production of components that can operate as sandwich waveguides and can be implemented in simple, cheap processes that produce robust fluidic structures.

Some of the implementations described above in relation to FIGS. 1-12 illustrate examples of a method that includes producing an article. The article includes a body with light-transmissive first and second wall parts; first and second inward surfaces and first and second outward surfaces on the first and second wall parts, respectively; and one or more light interface surfaces, each on one of the wall parts. The inward surfaces face each other and are separated by a fluidic region that can contain fluid, while the outward surfaces face away from the fluidic region; the inward and outward surfaces are all approximately parallel, but each of the light interface surfaces is not parallel to any of the inward and outward surfaces. The act of producing the article includes performing a complementary surface fabrication process to produce each of the inward and outward surfaces and a set of the light interface surfaces with a respective portion that has optical quality. The article is structured to operate as a sandwich waveguide with fluid in the fluidic region within the inward surfaces and with light entering the fluidic region through at least one of the set of light interface surfaces.

In specific implementations, the act of performing a complementary surface fabrication process can produce the inward surfaces, the outward surfaces, and the set of light interface surfaces concurrently; for example, they can all be produced in a single step. The complementary surface fabrication process can include at least one of molding, casting, and embossing, and it can include, for example, one of injection molding and hot embossing.

Some of the implementations described in relation to FIGS. 1-12 also illustrate examples of an article of manufacture that includes a body, inward surfaces, outward surfaces, and light interface surfaces as described above. The article is structured to operate as a sandwich waveguide as described above, and it includes a set of one or more complementary surface artifacts.

In specific implementations, each of the complementary surface artifacts can be in at least one of the body, the inward surfaces, the outward surfaces, and the set of light interface surfaces. The set of complementary surface artifacts can include the portions of the inward surfaces, outward surfaces, and set of light interface surfaces that have optical quality. The set of complementary surface artifacts can include at least one of an exposed artifact and a sub-surface artifact.

In further specific implementations, the article's first and second wall parts can be approximately equal in height. A device that includes the article can also include a cover part connected over the first and second wall parts; the article can also include, between the first and second inward surfaces, a base surface, and, along a length of the fluidic region, the inward surfaces, the base surface, and the cover part's lower surface can bound the fluidic region. The fluidic region can extend in a longitudinal direction between first and second open ends, and such a device can also include first and second ducting components connected to the article and cover part at the first and second open ends, respectively. The outward surfaces can be structured to provide approximately total internal reflection when operating as a sandwich waveguide, and the device can also include a photosensing component that senses light emanating from at least one of the outward surfaces. The device can also include a light source component providing light incident on at least one of the set of light interface surfaces.

In further specific implementations, a method can use an article as described above by positioning fluid in the fluidic region and causing the article to operate as a sandwich waveguide in which light propagates through the fluid. The act of causing the article to operate as a sandwich waveguide can include providing incident light on at least one of the light interface surfaces. The method can also include, while the article operates as a sandwich waveguide, photosensing light emanating from at least one of the outward surfaces. The act of positioning fluid can position analyte carried by the fluid in the fluidic region; the analyte can interact with the propagating light and, in response, can cause light to emanate from the fluidic region.

Some of the implementations described above in relation to FIGS. 1-12 also illustrate examples of an article of manufacture that includes an integrally formed body and, on the body, a surface. The surface includes a base area extending between first and second lateral borders, and first and second inward areas that meet the base area at the first and second lateral borders, respectively. Each of the first and second inward areas extends from the base area to a respective open edge, and at least a portion of each inward area has optical quality. The inward areas are approximately parallel, facing each other and being separated by a fluidic region that can contain fluid; along a length of the fluidic region, the base area and the first and second inward areas bound the fluidic region except between the open edges of the inward areas. The body and surface are structured to operate as a sandwich waveguide with fluid in the fluidic region between portions of the inward areas that have optical quality. The article includes a set of complementary surface artifacts, each in at least one of the body and the surface.

In specific implementations, each of the base area and the inward areas can be approximately planar, and each of the inward areas can be approximately perpendicular to the base area. The set of complementary artifacts can include the inward area portions that have optical quality, and can include at least one of an exposed artifact and a sub-surface artifact.

In further specific implementations, the body can include first and second wall parts, with the first and second inward areas being on the first and second wall parts, respectively; the surface can also include first and second outward areas on the first and second wall parts, respectively, each facing away from the fluidic region, and each having at least a portion that has optical quality and that is a complementary surface artifact. The inward and outward areas can all be approximately parallel. Each of the first and second wall parts can be light-transmissive between the portions of its inward and outward areas that have optical quality. The surface can also include light interface areas, each on one of the wall parts and not parallel to any of the inward and outward areas, and each having at least a portion with optical quality that is a complementary surface artifact; the body and surface can be structured to operate as an anti-resonant waveguide with fluid in the fluidic region and with light entering the fluidic region through at least one of the set of light interface areas. The wall parts can be approximately equal in height.

In further specific implementations, a device can include an article as described above and also a cover part connected to the surface, meeting and extending between the open edges of the inward areas; along the length of the fluidic region, the base area, the inward areas, and the cover part's lower surface can bound the fluidic region. In such a device, the fluidic region can extend between first and second open ends, and the device can also include first and second ducting components connected to the surface at the first and second open ends, respectively. A method of using an article as described above can include positioning fluid in the fluidic region and causing the body and surface to operate as a sandwich waveguide in which light propagates through the fluid.

Some of the implementations described above in relation to FIGS. 1-12 also illustrate examples of a method that includes producing an article with an integrally formed body and, on the body, a surface as described above. The act of producing the article includes performing a complementary surface fabrication process to produce the body and the surface. The body and surface are structured to operate as a sandwich waveguide with fluid in the fluidic region between portions of the inward areas that have optical quality.

In specific implementations, the body can include wall parts, with respective inward areas and outward areas as described above and with one or more light interface areas as described above; the act of performing a complementary surface fabrication process can produce the inward areas, the outward areas, and the set of light interface areas concurrently, or even in a single step. The act of performing a complementary surface fabrication process can include at least one of molding, casting, and embossing, and can include one of injection molding and hot embossing.

The exemplary implementations described above can therefore provide compact, inexpensive, and easy to manufacture components that can be used to perform operations such as spectrometry. For example, a portable, easy-to-use spectrometer could include an analyzer as described in U.S. patent application Ser. No. 11/316,660, entitled "Providing Light to Channels or Portions", and incorporated herein by reference in its entirety. In particular, these techniques can be used to produce chip-size spectrometers, allowing for implementation of fluorescence spectroscopy on a chip, as described in Schmidt, O., Bassler, M., Kiesel, P., Knollenberg, C., and Johnson, N., "Fluorescence Spectrometer-on-a-fluidic-chip", Lab on a Chip, 2007, DOI: 10.1039/b618879f, incorporated herein by reference. It is expected that fluidic structures as described above can be operated as sandwich waveguides to produce strong interaction between excitation light and analyte, allowing continuous excitation of a large volume of analyte. In addition, due to the simple and cheap manufacturing techniques as described herein, a lab-on-a-chip system could be produced at a price that would make it feasible as a disposable, single use product, an application in which anti-resonant waveguiding is expected to provide excellent results.

The exemplary implementations described above employ particular fabrication processes and materials to produce articles, structures, components, and parts with specific parameters and waveguide modes, but various other processes and materials could be used to produce items with various other parameters and modes, and with various other shapes, dimensions, or other numerical or qualitative characteristics other than those illustrated and described above. For example, the lists of materials described above include many that are currently known to be appropriate for complementary surface fabrication, but it is foreseeable that new materials will be developed that will be appropriate for such processes, and also that new types of complementary surface fabrication processes will be developed. Also, specific types of light sources and photosensing components are mentioned above, but any appropriate light source component or photosensing component could be used, including types hereafter developed. In addition, various dimensions could be used, as would be appropriate for different photon energies or for different waveguide propagation modes.

Some of the above exemplary implementations include production of integrally formed bodies with straight waveguides, but the invention could be implemented with bodies that have waveguides of other appropriate shapes, including, to some extent, inward surfaces that depart to a limited extent from being straight, and possibly also might depart to a limited extent from being parallel whether or not they are straight or planar. Similarly, the above-described exemplary implementations include light interface areas that are approximately planar, but various other surface shapes could be employed to receive incident light, including multi-faceted surfaces or curved surfaces, and various techniques for providing incident light could be employed to operate such a structure, using any appropriate angle of incidence.

Some of the above exemplary implementations employ an arrangement of one or more light sources and one or more photosensing components relative to a fluidic structure that includes one or more channels and may include a stack of articles, each of which can be operated as a sandwich waveguide within which fluid moves and carries objects, and a wide variety of such arrangements could be made within the scope of the invention. The particular arrangements described above are only illustrative, and it would be possible to change the number, positions, and orientations of light sources and photosensing components in a wide variety of ways consistent with articles produced as described above.

The above exemplary implementations are described in terms of fluidic structures and enhanced light-target interaction to obtain fluorescence or scattering. In general, however, the techniques described above could also be used to produce articles in which light emanates as a result of other operations, such as self-emission, auto-fluorescence, other types of fluorescence, photo-luminescence, chemo-fluorescence, inelastic or elastic scattering, absorption, and so forth.

Depending on the mechanism, different arrangements of light sources or photosensing components may be preferable. For fluorescence measurements, for example, it is often preferable to have an excitation light source at a waveguide's light interface surface and a photosensing component along the outward surface of the waveguide; alternatively, excitation light could be coupled through the outward surface and fluorescence light could propagate through the waveguide to the interface surface where it could be detected by a photosensing component. For auto-fluorescing or self-emitting analytes, it is not necessary to excite analytes with a light source; in these cases, a photosensing component either at the outward surface or at the interface surface can detect emitted light. Similarly, if chemo-fluorescence is created by mixing substances in a channel, no light source is required to excite analytes; on the other hand, the structure can be used to start a reaction by photo-activation, in which case light from a light source attached to the interface surface can propagate through the waveguide to a substance in the channel that requires activation energy-no photosensing components would be required for an application with only photo-activation. For absorption measurements, it is possible to use two light interface surfaces, one at an end of the channel where incident light from an attached light source couples into the waveguide and another at an opposite end of the channel where remaining light after absorption is coupled out, sensed by a photosensing component, and analyzed.

The technique of anti-resonant waveguiding, described above, is only one type of sandwich waveguiding, and the techniques described above could be used with other types of sandwich waveguiding. Furthermore, various parameters could be adjusted to obtain anti-resonant waveguiding of various types, including dimensions and angles of incidence.

The above exemplary implementations generally involve production and use of articles following particular operations, but different operations could be performed, the order the operations could be modified, and additional operations could be added within the scope of the invention.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method comprising:
    producing an article that includes:
        a body with light-transmissive first and second wall parts;
        first and second inward surfaces on the first and second wall parts, respectively; the inward surfaces facing each other and being separated by a fluidic region that can contain fluid;
        first and second outward surfaces on the first and second wall parts, respectively; each outward surface facing away from the fluidic region; the inward and outward surfaces all being approximately parallel; and
        one or more light interface surfaces, each light interface surface being on one of the first and second wall parts and not being parallel to any of the inward and outward surfaces;
    the act of producing the article including:
        performing a complementary surface fabrication process to produce each of the inward and outward surfaces and a set of at least one of the light interface surfaces with a respective portion that has optical quality; the article being structured to operate as a sandwich waveguide with fluid in the fluidic region between the inward surfaces and with light entering the fluidic region through at least one of the set of light interface surfaces.

2. The method of claim 1 in which the act of performing a complementary surface fabrication process produces the first and second inward surfaces, the first and second outward surfaces, and the set of light interface surfaces concurrently.

3. The method of claim 2 in which the act of performing a complementary surface fabrication process produces the first and second inward surfaces, the first and second outward surfaces, and the set of light interface surfaces in a single step.

4. The method of claim 1 in which the act of performing a complementary surface fabrication process includes at least one of molding, casting, and embossing.

5. The method of claim 1 in which the act of performing a complementary surface fabrication process includes one of injection molding and hot embossing.

6. The method of claim 1 in which the act of performing a complementary surface fabrication process includes injection molding a non-solid material, the non-solid material including at least one of acetal, nylon, polypropylene, polycarbonate, acrylonitrile butadiene styrene, polybutylene, polystyrene, and acrylic.

7. The method of claim 1 in which the act of performing a complementary surface fabrication process includes hot embossing a non-solid material, the non-solid material including at least one of polymethyl methacrylate, polycarbonate, polyether imide, polytetrafluoroethylene, and polyetheretherketone.

8. An article of manufacture comprising:
    a body with light-transmissive first and second wall parts;
    first and second inward surfaces on the first and second wall parts, respectively; the inward surfaces facing each other and being separated by a fluidic region that can contain fluid; at least a portion of each of the inward surfaces having optical quality;
    first and second outward surfaces on the first and second wall parts, respectively; each outward surface facing away from the fluidic region; at least a portion of each outward surface having optical quality; the inward and outward surfaces all being approximately parallel; and
    one or more light interface surfaces, each light interface surface being on one of the first and second wall parts and not being parallel to any of the inward and outward surfaces; each of a set of the light interface surfaces having at least a portion with optical quality;
    the article being structured to operate as a sandwich waveguide with fluid in the fluidic region between the inward surfaces and with light entering the fluidic region through at least one of the set of light interface surfaces; the article including a set of one or more complementary surface artifacts.

9. The article of claim 8 in which each of the complementary surface artifacts is in at least one of the body, the first and second inward surfaces, the first and second outward surfaces, and the set of light interface surfaces.

10. The article of claim 9 in which the set of complementary surface artifacts includes the portions of the first and second inward surfaces, of the first and second outward portions, and of the set of light interface surfaces that have optical quality.

11. The article of claim 8 in which the set of complementary surface artifacts includes at least one of an exposed artifact and a sub-surface artifact.

12. The article of claim 8 in which the first and second wall parts are approximately equal in height.

13. A device that includes the article of claim 8, the device further including:
    a cover part connected over the first and second wall parts.

14. The device of claim 13 in which the fluidic region extends in a longitudinal direction between first and second open ends; the device further including:
    first and second ducting components connected to the article and cover part at the first and second open ends, respectively.

15. The device of claim 13 in which the first and second outward surfaces are structured to provide approximately total internal reflection when the article is operating as a sandwich waveguide; the device further including:
    a photosensing component that senses light emanating from at least one of the first and second outward surfaces.

16. The device of claim 13, further including:
    a light source component that provides light that is incident on at least one of the set of light interface surfaces.

17. A method of using the article of claim 8, the method comprising:
positioning fluid in the fluidic region; and
causing the article to operate as a sandwich waveguide in which light propagates through the fluid in the fluidic region.

18. The method of claim 17 in which the act of causing the article to operate as a sandwich waveguide includes providing incident light on at least one of the light interface surfaces.

19. The method of claim 17, further comprising:
while the article operates as a sandwich waveguide, photosensing light emanating from at least one of the first and second outward surfaces.

20. The method of claim 17 in which the act of positioning fluid includes positioning analyte carried by the fluid in the fluidic region, the analyte interacting with the propagating light and, in response, causing light to emanate from the fluidic region.

21. An article of manufacture comprising:
an integrally formed body; and
on the body, a surface that includes:
a base area extending between first and second lateral borders; and
first and second inward areas that meet the base area at the first and second lateral borders, respectively, each of the first and second inward areas extending from the base area to a respective open edge;
at least a portion of each of the inward areas having optical quality;
the first and second inward areas being approximately parallel, facing each other and being separated by a fluidic region that can contain fluid; along a length of the fluidic region, the base area and the first and second inward areas bounding the fluidic region except between the open edges of the first and second inward areas;
the body and surface being structured to operate as a sandwich waveguide with fluid in the fluidic region between portions of the inward areas that have optical quality;
the article including a set of one or more complementary surface artifacts, each of the artifacts being in at least one of the body and the surface.

22. A method comprising:
producing an article that includes:
an integrally formed body; and
on the body, a surface that includes:
a base area extending between first and second lateral borders; and
first and second inward areas that meet the base area at the first and second lateral borders, respectively, each of the first and second inward areas extending from the base area to a respective open edge;
the first and second inward areas being approximately parallel, facing each other and being separated by a fluidic region that can contain fluid; along a length of the fluidic region, the base area and the first and second inward areas bounding the fluidic region except between the open edges of the first and second inward areas;
the act of producing the article including:
performing a complementary surface fabrication process to produce the body and the surface with each of the inward areas having a respective portion that has optical quality; the body and surface being structured to operate as a sandwich waveguide with fluid in the fluidic region between portions of the inward areas that have optical quality.

23. An article of manufacture comprising:
an integrally formed body; and
on the body, a surface that includes:
a base area extending between first and second lateral borders; and
first and second inward areas that meet the base area at the first and second lateral borders, respectively, each of the first and second inward areas extending from the base area to a respective open edge;
at least a portion of each of the inward areas having optical quality;
the first and second inward areas being approximately parallel, facing each other and being separated by a fluidic region that can contain fluid; along a length of the fluidic region, the base area and the first and second inward areas bounding the fluidic region except between the open edges of the first and second inward areas;
the body including light-transmissive first and second parts, the first and second inward areas being on the first and second parts, respectively; the body and surface being structured to operate as a waveguide with fluid in the fluidic region between portions of the inward areas that have optical quality, the fluid having lower refractive index than the first and second parts;
the article including a set of one or more complementary surface artifacts, each of the artifacts being in at least one of the body and the surface.

24. The article of claim 23 in which each of the base area and the first and second inward areas is approximately planar, each of the first and second inward areas being approximately perpendicular to the base area.

25. The article of claim 23 in which the first and second parts are wall parts; the surface further including:
first and second outward areas on the first and second parts, respectively; each outward area facing away from the fluidic region; at least a portion of each outward area having optical quality, each outward area portion with optical quality being a complementary surface artifact; the inward and outward areas all being approximately parallel.

26. The article of claim 25 in which the surface further includes:
one or more light interface areas, each light interface area being on one of the first and second parts and not being parallel to any of the inward and outward areas; each of a set of the light interface areas having at least a portion with optical quality, each light interface area portion with optical quality being a complementary surface artifact;
the body and surface being structured to operate as an anti-resonant waveguide with fluid in the fluidic region and with light entering the fluidic region through at least one of the set of light interface areas.

27. A method of producing the article of claim 23, the method comprising:
performing a complementary surface fabrication process to produce the body and the surface with each of the inward areas having a respective portion that has optical quality.

28. The method of claim 27 in which the first and second parts are wall parts; the surface further including:
first and second outward areas on the first and second parts, respectively; each outward area facing away from the fluidic region; and one or more light interface areas, each light interface area being on one of the first and second parts and not being parallel to any of the inward and outward areas;

the act of performing a complementary surface fabrication process producing the first and second inward areas, the first and second outward areas, and the set of light interface areas concurrently.

29. The method of claim 28 in which the act of performing a complementary surface fabrication process produces the first and second inward areas, the first and second outward areas, and the set of light interface areas in a single step.

* * * * *